United States Patent [19]
Crawford et al.

[11] Patent Number: 5,438,602
[45] Date of Patent: Aug. 1, 1995

[54] CORRECTION OF CT ATTENUATION DATA USING FAN BEAM REPROJECTIONS

[75] Inventors: Carl R. Crawford, Milwaukee, Wis.; Cameron J. Ritchie, Seattle, Wash.

[73] Assignee: General Electric Company, Milwaukee, Wis.

[21] Appl. No.: 172,660

[22] Filed: Dec. 23, 1993

[51] Int. Cl.⁶ .................. A61B 6/03; G01N 23/083
[52] U.S. Cl. .......................... 378/4; 378/15; 378/901; 364/413.16
[58] Field of Search ............... 364/413.16, 413.19, 364/413.21; 378/4, 15, 901

[56] References Cited

U.S. PATENT DOCUMENTS

| | | | |
|---|---|---|---|
| 4,222,104 | 9/1980 | Moore | 364/413.17 |
| 4,616,318 | 10/1986 | Crawford | 362/413.2 |
| 4,626,991 | 12/1986 | Crawford et al. | 364/413.21 |
| 4,709,333 | 11/1987 | Crawford | 364/413.14 |
| 4,714,997 | 12/1987 | Crawford et al. | 364/413.21 |
| 5,008,822 | 4/1991 | Brunnett et al. | 364/413.21 |
| 5,243,664 | 9/1993 | Tuy | 382/6 |

OTHER PUBLICATIONS

*An Improved Algorithm For Reprojecting Rays Through Pixel Images*, IEEE Transactions on Medical Imaging, vol. MI-1, No. 3, Nov. 1982, pp. 192-196, Peter M. Joseph.

*Reprojection Using A Parallel Backprojector*, Am. Assoc. Phys. Med., Med. Phys, 13(4), Jul./Aug. 1986, pp. 480-483, Carl R. Crawford.

*A Method for Correcting Bone Induced Artifacts in Computed Tomography Scanners*, Journal of Computer Assisted Tomography, 2:100-108, Jan. 1978, Peter M. Joseph & Robin D. Spital.

*A Simple Computational Method For Reducing Streak Artifacts In CT Images*, Computerized Tomography, vol. 4, Aug. 1979, pp. 67-71, G. Henrich.

*An Algorithm For The Reduction Of Metal Clip Artifacts In CT Reconstruction*, Medical Physics, vol. 8, No. 6, Nov./Dec. 1981, G. H. Glover & N. J. Pelc.

*High Speed Reprojection and its Application*, SPIE, vol. 914 Medical Imaging II (1988), pp. 311-318, Carl R. Crawford, et al.

*Primary Examiner*—Paul M. Dzierzynski
*Assistant Examiner*—David Veron Bruce

[57] ABSTRACT

In an x-ray computed tomography system which acquire x-ray attenuation data using a fan beam of radiation, corrections for beam hardening are made by reprojecting the CT image data. The reprojection computations are reduced by rotating and warping the CT image data, and then performing a parallel reprojection along columns of data.

9 Claims, 3 Drawing Sheets

CORRECTION OF CT ATTENUATION DATA USING FAN BEAM REPROJECTIONS

BACKGROUND OF THE INVENTION

The present invention relates to computed tomography (CT) imaging apparatus; and more particularly, the correction of acquired x-ray attenuation data using image reprojection.

In a current computed tomography system, an x-ray source projects a fan-shaped beam, which is collimated to lie within an X-Y plane of a Cartesian coordinate system, termed the "imaging plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce the transmission profile.

The source and detector array in a conventional CT system are rotated on a gantry within the imaging plane and around the object so that the angle at which the x-ray beam intersects the object constantly changes. A group of x-ray attenuation measurements from the detector array at a given angle is referred to as a "view" or "projection," and a "scan" of the object comprises a set of views made at different angular orientations during one revolution of the x-ray source and detector. In a 2D scan, data are processed to construct an image that corresponds to a two dimensional slice taken through the object. The prevailing method for reconstructing an image from 2D data is referred to in the art as the filtered backprojection technique. This process converts the attenuation measurements from a scan into integers called "CT numbers" or "Hounsfield units", which are used to control the brightness of a corresponding pixel on a cathode ray tube display.

To reconstruct an accurate image from the attenuation measurements, the logarithm of the measurement should represent the sum, or line integral, of the linear attenuation coefficients along the x-ray beam. This would be true if a monoenergetic x-ray source were used but in practice, inaccuracies are introduced because broadband x-ray sources are used and the attenuation coefficients of tissues vary nonlinearly as a function of beam energy. "Beam hardening" corrections are made to the attenuation measurements to offset these errors, but these usually offset only first order estimates of the measurement errors.

An iterative beam hardening correction method has been proposed by P.M. Joseph, et al., "A Method for Correcting Bone Induced Artifacts in Computed Tomography Scanners," JCAT, Vol. 2, No. 1, pp. 100-108, 1978, which corrects for higher order beam hardening effects. However, this method requires that a modified version of the image be reprojected back to the separate views so that the corrections can be applied to the x-ray measurement made by each detector channel. Such reprojection of an image is very computation intensive, particularly when the image is acquired with a fan beam. There exists a need for faster and less complex fan beam reprojection techniques so that iterative beam hardening corrections can be employed in commercially available CT systems. Also, such reprojections are required in streak suppression methods such as that described by G. Henrich, "A Simple Computational Method For Reducing Streak Artifacts in CT Images," Computerized Tomography, Vol. 4, pp. 67-71, 1980; and in artifact removal methods such as that proposed for metal clips by G. H. Glover and N.J. Pelc, "An Algorithm for the Reduction of Metal Clip Artifacts in CT Reconstructions," Med. Phys., vol. 8, pg. 799, 1981.

SUMMARY OF THE INVENTION

The present invention relates to a method for reprojecting image data into a set of fan beam projections so that corrections can be calculated therefrom for application to the originally acquired fan beam projection data. More specifically, the method includes: rotating the image data by an amount ($\beta$) corresponding to the angle of a desired fan beam projection, warping the rotated image data to change the shape of objects depicted therein; and reprojecting the rotated and warped image data along parallel lines to form a fan beam projection. The method is repeated for each desired fan beam projection.

A general object of the invention is to reduce the computations necessary to reproject modified CT image data into fan beam projections. The rotation and warping operations can be less complex than fan beam reprojection calculations. In addition, the rotation step reduces the reprojection along parallel lines to the simple summing of data in columns of the rotated and warped array.

A more specific object of the invention is to enable iterative corrections to be made to CT image data acquired with a fan beam. The present invention enables image processors on commercially available CT systems to quickly reproject the fan beam projections required to calculate corrections from the CT image data acquired using a fan beam. Beam hardening corrections can be made in one or more iterations of the back projection, reprojection and correction cycle.

GENERAL DESCRIPTION OF THE INVENTION

Figure 1:
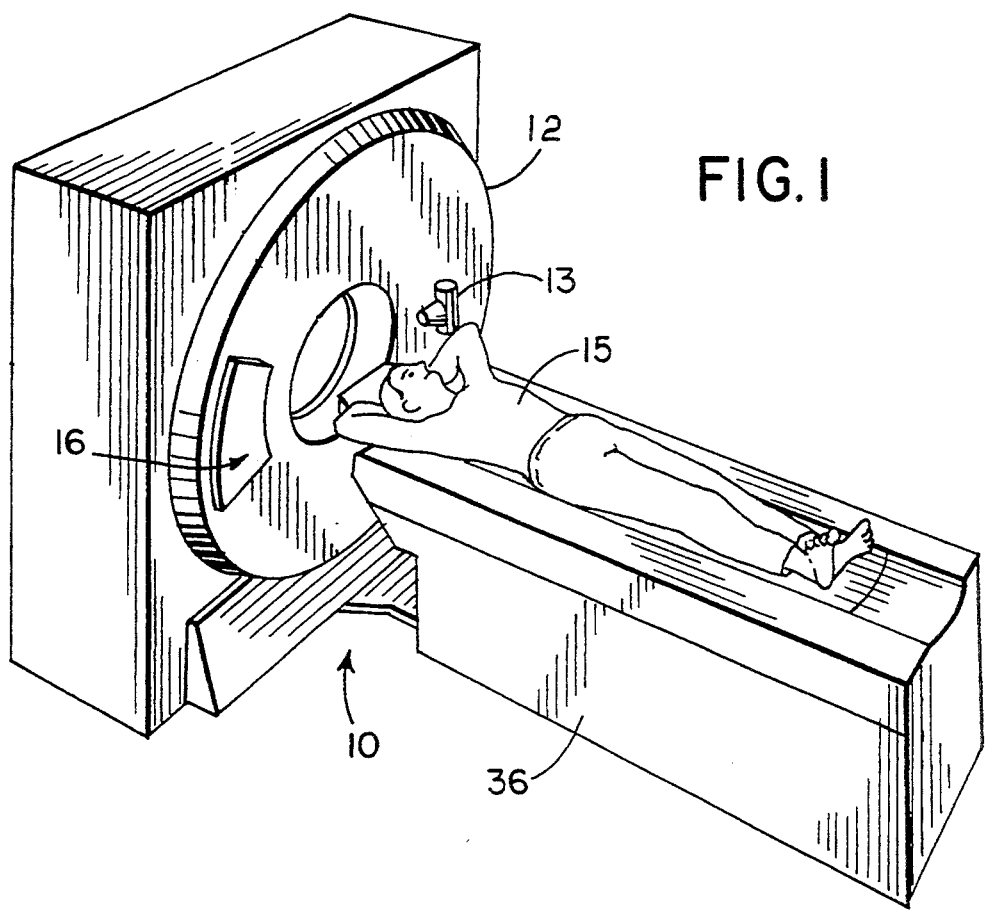
FIG. 1 is a pictorial view of a CT imaging system in which the present invention may be employed.

The present invention is based on the realization that fan beam (FB) reprojection can be generated using a parallel beam (PB) reprojection of a warped image. The resulting parallel beam reprojection reduces to either a column or row collapse if the image is also rotated before the warp and the reprojection. The mathematical expression of these steps in the method will now be described for continuously sampled functions. This description is then extended to apply to discretely sampled images such as those produced in the preferred embodiment described below.

Let $p_\theta(t)$ be the PB projection of an image $f(x,y)$ for the path $t = x \cos\theta - y \sin\theta$. The analytic expression for the projection is:

$$p_\theta(t) = \int_{-\infty}^{\infty} \int_{-\infty}^{\infty} f(x,y)\delta(t - x\cos\theta + y\sin\theta)dx\,dy. \quad (1)$$

Consider the $(x',y')$-space that is obtained by rotating $(x, y)$ by $\theta$:

$$\begin{pmatrix} x' \\ y' \end{pmatrix} = \begin{pmatrix} \cos\theta & -\sin\theta \\ \sin\theta & \cos\theta \end{pmatrix} \begin{pmatrix} x \\ y \end{pmatrix} = \begin{pmatrix} x\cos\theta - y\sin\theta \\ x\sin\theta + y\cos\theta \end{pmatrix} \quad (2)$$

or $$\begin{aligned} x &= x'\cos\theta + y'\sin\theta \\ y &= -x'\sin\theta + y'\cos\theta. \end{aligned} \quad (3)$$

Now substitute equation (2) into equation (1)

$$p_\theta(t) = \int_{-\infty}^{\infty}\int_{-\infty}^{\infty} f(x'\cos\theta + y'\sin\theta, -x'\sin\theta + y'\cos\theta)\,\delta(t - x')\,dx'\,dy' \quad (4)$$

which can be simplified to $$p_\theta(t) = \int_{-\infty}^{\infty} f(t\cos\theta + y\sin\theta, -t\sin\theta + y\cos\theta)\,dy \quad (5)$$

where the prime y' has been dropped.

Figure 3:
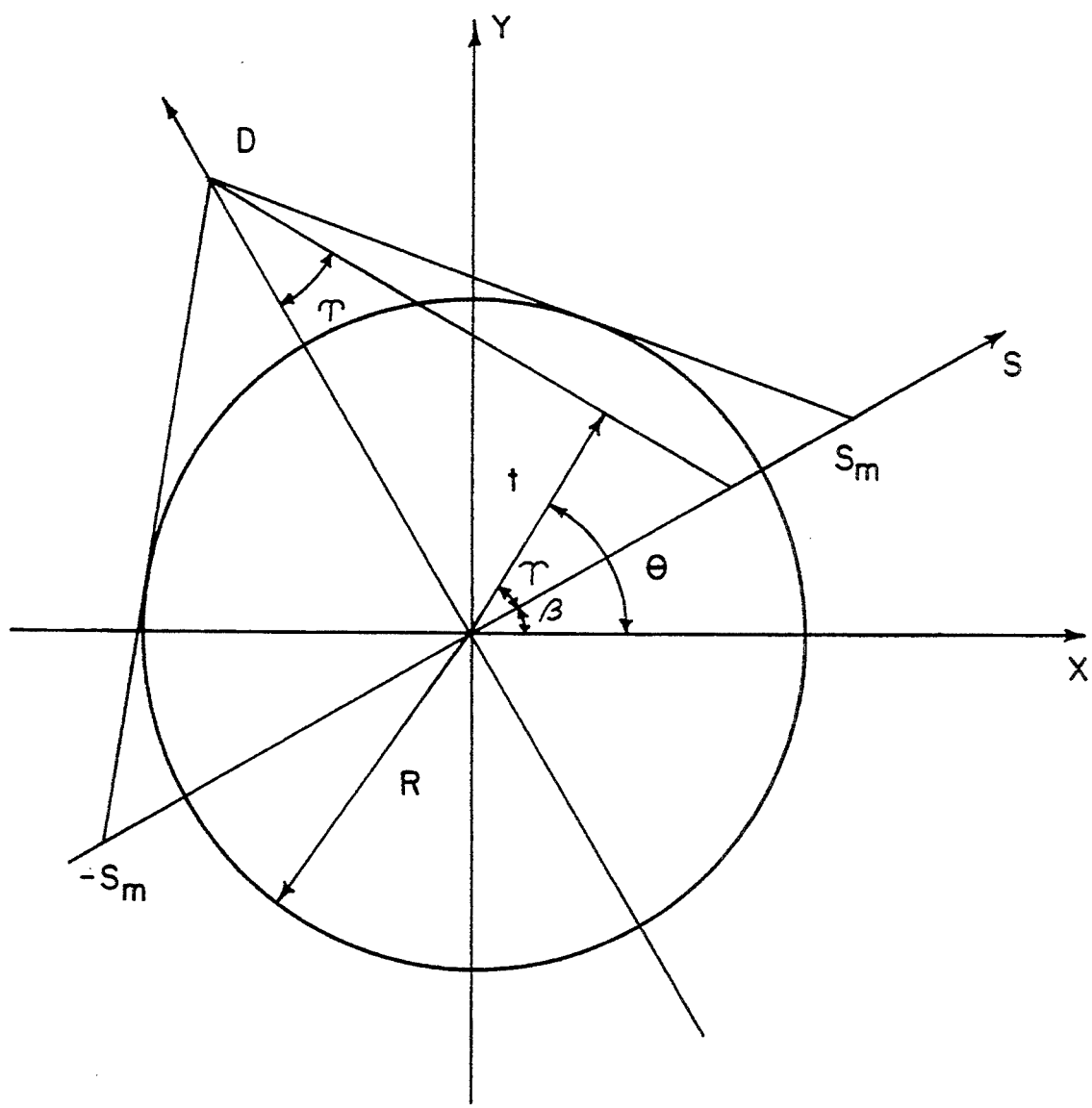
FIG. 3 is a schematic representation of scanner geometry used in deriving equations employed to practice the present invention.

Let $r_\beta(s)$ be the FB projection of $f(x,y)$ where the projection or rotation angle is $\beta$ and s is the position of a detector. The geometry of the FB projection is shown in FIG. 3. In this figure an equi-spaced detector array is shown. This detector array is shown passing through the origin for mathematical convenience, but it can be appreciated that the detector array is actually spaced from the origin of the imaging system. Implicit to a FB projection is the source-to-center distance, which is denoted D. It can be shown that FB and PB projections are related as follows:

$$p_\theta(t) = r_\beta(s) \quad (6)$$
for
$$t = DsZ$$

$$\theta = \beta + \tan^{-1}\frac{s}{D} \quad (7)$$

and where $$Z = \frac{1}{\sqrt{D^2 + s^2}} \quad (8)$$

For the moment, consider the FB projection at $\beta=0$. The mathematical formula for this projection is obtained by inserting equations (6) and (7) into equation (5).

$$r_0(s) = \int_{-\infty}^{\infty} f(D^2Z^2s + ysZ, -Ds^2Z^2 + yDZ)dy. \quad (9)$$

Consider the following change of variables $$\eta = -Ds^2Z^2 + yDZ \quad (10)$$

which leads to $$y = \frac{\eta + Ds^2Z^2}{DZ} \quad (11)$$

and $$d\eta = DZ\,dy. \quad (12)$$

Using equations (10–12), equation (9) reduces to $$r_0(s) = \frac{1}{DZ}\int_{-\infty}^{\infty} f'(s,\eta)d\eta \quad (13)$$

where $$f'(s,\eta) = f(x,y) \quad (14)$$

and where $$x = (D + \eta)\frac{s}{D} \quad (15)$$

$$y = \eta.$$

The function f' is a warped version of the source function f. More specifically the function is expanded and compressed along lines of constant Y. The expansion takes place for positive values of Y and compression elsewhere. The integral equation (13) indicates that the FB projection at $\beta=0$ is obtained by taking the PB projection of the warped version of the source function. The PB projection is calculated at $\theta=0$. The warping step can be viewed as translating image pixels which lie on a set of rays emanating from a single point, or vertex, to a corresponding set of parallel rays.

The development of equation (13) was for $\beta=0$. It can be shown, however, that equation (13) can be used to find the FB reprojection using the PB projection of the warped function at any rotation angle if the image function is first rotated by the negative of the rotation angle. This result is particularly useful if equation (13) is being used for FB reprojection because PB reprojections at zero rotation angle reduces to a simple projection along one of the two main axes. Such projections are denoted as column and row collapses.

The above indicates that the image should first be rotated by the projection angle, $\beta$, using equation (3) and then warped using equation (14). The rotation and warping operations can be combined into one operation if necessary as follows:

$$x = \left[(D + \eta)\frac{s}{D}\right]\cos\beta + \eta\sin\beta \quad (16)$$

$$Y = -\left[(D + \eta)\frac{s}{D}\right]\sin\beta + \eta\cos\beta.$$

Equation (13) shows that PB projections of the warped object have to be scaled by $1/DZ$ to make them equivalent to FB projections. The scaling can be avoided by using the following change of variables instead of those in equation (10):

$$\eta = -s^2Z + Y \quad (17)$$

which leads to the following relationship between FB and PB projections:

$$r_0(s) = \int_{-\infty}^{\infty} f(s,\eta)d\eta \qquad (18)$$

where $$f(s,\eta) = f(x,y) \qquad (19)$$

and where $$x = (1+Z\eta)s \quad y = \eta + s^2 Z \qquad (20)$$

For practical application in commercial CT systems, equations (13) and (16) must be adapted to reproject an image comprised of a two-dimensional array of image sample values. The image covers a circular field-of-view of radius R and it has N by N samples. The sampled image, F(i,j), is related to the continuous image, f(x,y) as follows $$F(i,j) = f(x,y), \quad 0 \leq i, j \leq N-1 \qquad (21)$$

for $$x = -R + i\delta_p + \delta_p/2 \qquad (22)$$

and $$y = R - j\delta_p + \delta_p/2 \qquad (23)$$

where $\delta_p = 2R/N$.

It can be seen in FIG. 3 that discrete samples of the FB reprojection in the s coordinate system are required in the range $-s_m < s < s_m$, where $$s_m = \frac{DR}{\sqrt{D^2 - R^2}}. \qquad (24)$$

Assume that M equally spaced samples are desired. Then the sampled reprojection, $R_\beta(k)$, can be related to the continuous projection, $r_\beta(s)$, as follows $$R_\beta(k) = r_\beta(s), \quad 0 \leq k \leq M-1 \qquad (25)$$

for $$s = -s_m = +k\delta_r + \delta_r/2 \qquad (26)$$

where $\delta_r = 2s_m/M$.

The sampled warped object, F'(k,l) can be obtained from the original unwarped and sampled image function, F(i,J), where l=j, using the following steps for each pixel and for a specific rotational angle, $\beta$:

1. Calculate s using equation (26);
2. Calculate $\eta$ using equation (23) noting that $\eta = Y$ from equation (15);
3. Calculate the xy-coordinate using equation (16); and
4. Using the results of the previous step, calculate the coordinates, i and j, of the pixel in the original image using equations (22) and (23). In general, the resulting values of i and j will not be integers. Bilinear interpolation can be used to find the value of the image at the desired location.

Finally, the FB reprojection at the angle $\beta$ is obtained by approximating the integral equation (13) with a summation $$R_\beta(k) \approx \frac{\delta_p}{DZ} \sum_{l=0}^{M-1} F(k,l) \qquad (27)$$

where Z is found using equations (8) and (26).

DESCRIPTION OF THE PREFERRED EMBODIMENT

Figure 2:
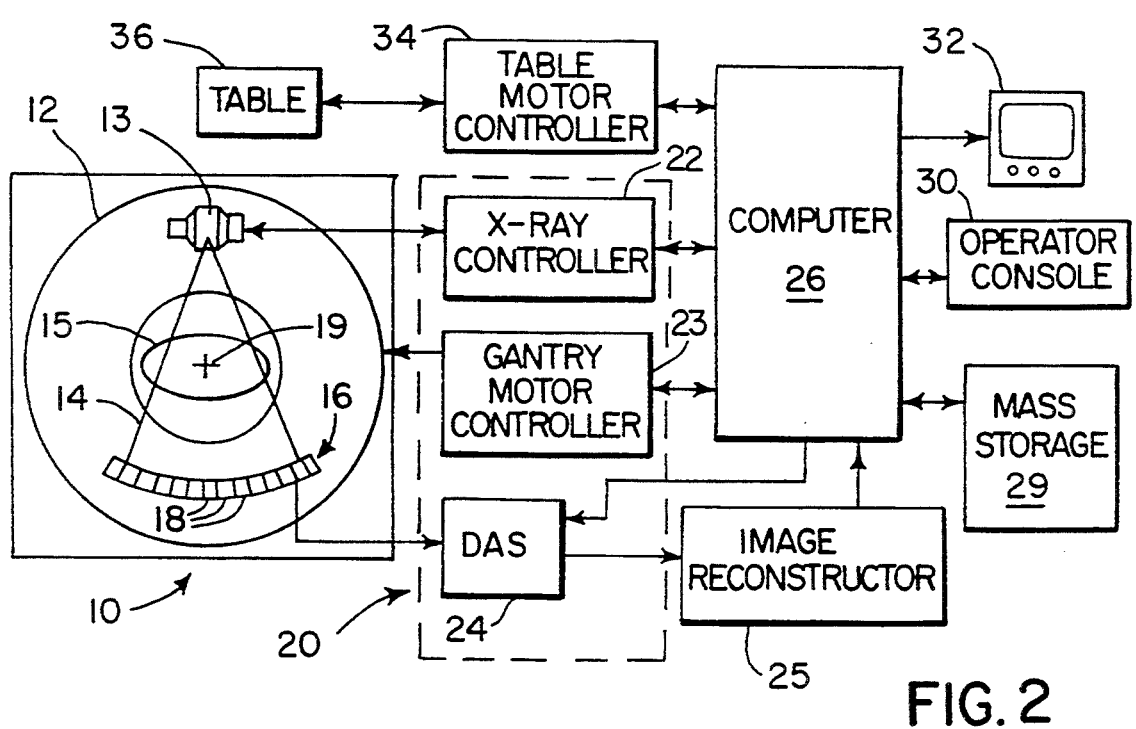
FIG. 2 is a block schematic diagram of the CT imaging system.

With initial reference to FIGS. 1 and 2, a computed tomography (CT) imaging system 10 includes a gantry 12 representative of a "third generation" CT scanner. Gantry 12 has an x-ray source 13 that projects a fan beam of x-rays 14 toward a detector array 16 on the opposite side of the gantry. The detector array 16 is formed by a number of detector elements 18 which together sense the projected x-rays that pass through a medical patient 15. Each detector element 18 produces an electrical signal that represents the intensity of an impinging x-ray beam and hence the attenuation of the beam as it passes through the patient. During a scan to acquire x-ray projection data, the gantry 12 and the components mounted thereon rotate about a center of rotation 19 located within the patient 15.

The rotation of the gantry and the operation of the x-ray source 13 are governed by a control mechanism 20 of the CT system. The control mechanism 20 includes an x-ray controller 22 that provides power and timing signals to the x-ray source 13 and a gantry motor controller 23 that controls the rotational speed and position of the gantry 12. A data acquisition system (DAS) 24 in the control mechanism 20 samples analog data from detector elements 18 and converts the data to digital signals for subsequent processing. An image reconstructor 25, receives sampled and digitized x-ray data from the DAS 24 and performs high speed image reconstruction according to the method of the present invention. The reconstructed image is applied as an input to a computer 26 which stores the image in a mass storage device 29.

The computer 26 also receives commands and scanning parameters from an operator via console 30 that has a keyboard. An associated cathode ray tube display 32 allows the operator to observe the reconstructed image and other data from the computer 26. The operator supplied commands and parameters are used by the computer 26 to provide control signals and information to the DAS 24, the x-ray controller 22 and the gantrymotor controller 23. In addition, computer 26 operates a table motor controller 34 which controls a motorized table 36 to position the patient 15 in the gantry 12.

Figure 4:
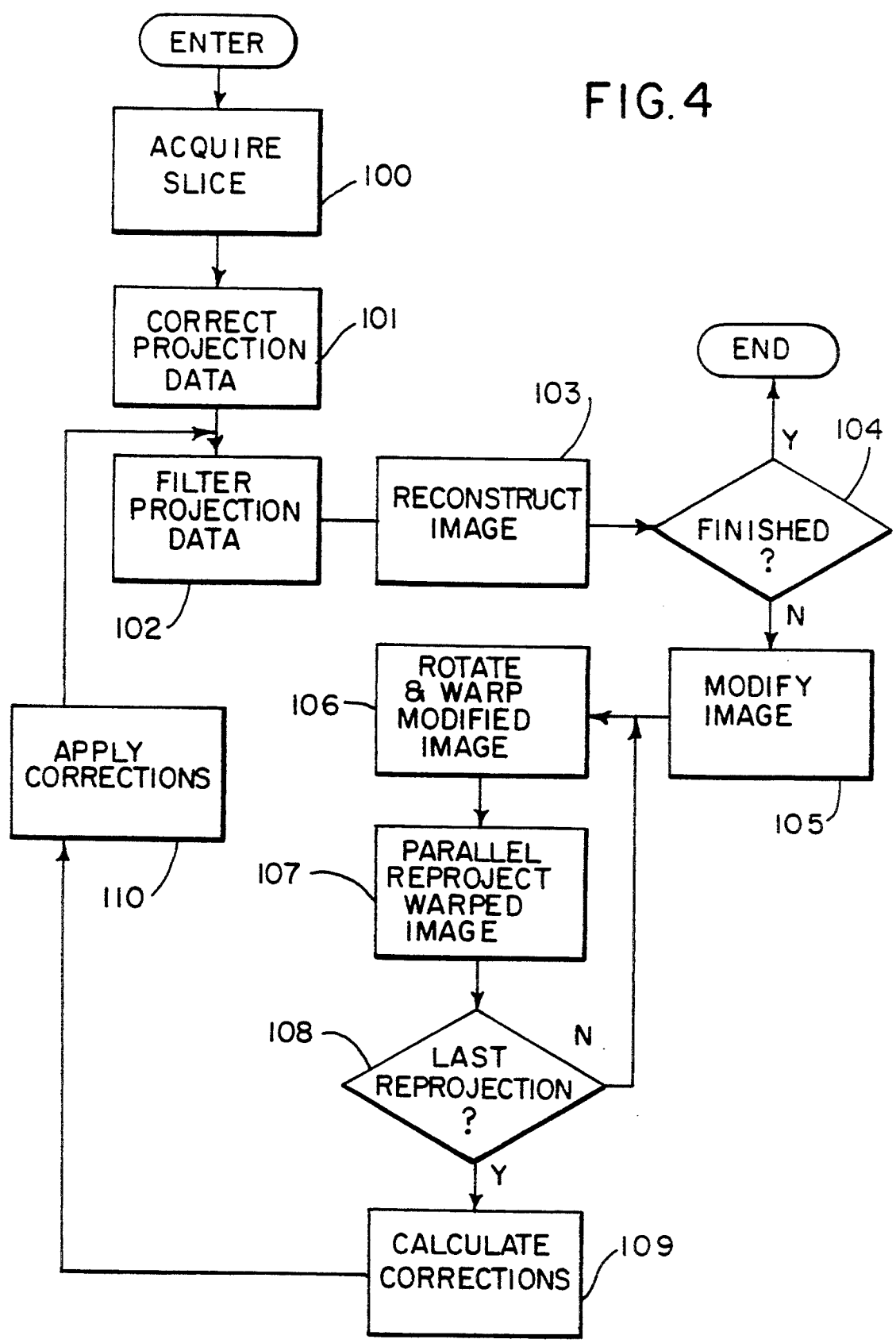
FIG. 4 is a flow chart of a program executed by the CT imaging system of FIG. 2 to carry out the present inventions.

The present invention is carried out by the CT system of FIG. 2 under the direction of a program executed by the computer 26. This method will now be described with reference to the flow chart in FIG. 4. After each slice of data has been acquired as indicated at process block 100 and corrected for "dark currents," for uneven detector channel sensitivities and gains, and for variations in beam intensity during the scan, a beam hardening correction is made to each projection as indicated at process block 101. This first order correction is made assuming that the x-ray beams are attenuated by soft tissues as described, for example, in the above-cited P.M. Joseph, et al. publication. Each set of projection data, or view, is then filtered as indicated at process block 102 as a prelude to image reconstruction at 103 using the well known back projection technique. As a result, an N by N array of CT numbers are produced and are displayed to the operator as an image of the slice.

The process may end at this juncture, as indicated by decision block 104, in those instances in which artifacts caused by bone tissue are not of concern. However, the present invention is applied when it is determined that further beam hardening corrections are required to account for bone tissue. For example, in a head scan or spine scan where large amounts of bone are present, further correction is always performed. As indicated at process block 105, the first step in this process is to modify the reconstructed image by filtering out samples corresponding to soft tissues. This is achieved by setting to zero all image pixels in the N by N array which have a CT number below that of bone. As indicated at process block 106, the resulting bone image is then rotated and warped using the above equation (16) as modified for use with the sampled bone image as described above. A parallel reprojection of the rotated and warped image at the gantry angles $\delta$ is then performed at process block 107 using the above equation (27). When bone reprojections at each of the original gantry angles have been produced, as detected at decision block 108, beam hardening corrections are calculated for each bone reprojection as indicated at process block 109. These corrections are made, for example, as described in the above-cited P.M. Joseph et al. publication, and the resulting corrections are applied to each of the previously corrected sets of projection data as indicated at process block 110. The resulting projection data has now been corrected for beam hardening assuming 100% soft tissue, and corrected again for beam hardening to account accurately for the presence of bone tissue.

The corrected projections are filtered at 102 and backprojected at 103 to produce another image. The process can be repeated any number of times to further refine the image, but in practice, one iteration through the reprojection process has been found sufficient in most clinical applications.

Although the above description applies to the equi-spaced detector array of FIG. 3, similar mathematics apply to a curved, or equi-angle detector array as shown in FIG. 2. The invention is also equally applicable to fourth and fifth generation CT imaging systems. The invention is also applicable to other imaging modalities which employ a fan beam, such as single photon emission computed tomography (SPECT).

We claim:

1. In an imaging system which acquires a plurality of fan beam projections during a scan and which reconstructs the fan beam projections to produce image data, a method comprising:
    a) reprojecting the image data to produce a fan beam reprojection at an angle $\beta$ by;
        i) warping the image data by translating image data along a set of lines emanating from the vertex of a fan beam to a corresponding set of parallel lines; and
        ii) reprojecting the warped image data along said set of parallel lines; and
    b) repeating step (a) at different angles $\beta$ to produce a corresponding set of fan beam reproductions.

2. The method as recited in claim 1 in which the image data is modified before being reprojected and the method includes:
    c) calculating corrections using the set of fan beam reproductions;
    d) applying the corrections to the plurality of fan beam projections; and
    e) reconstructing an image using the corrected fan beam projections.

3. The method as recited in claim 1 in which the imaging system is an x-ray CT system.

4. The method as recited in claim 2 in which the image system is an x-ray CT system and an imaging is reconstructed by backprojecting the corrected fan beam projections.

5. The method as recited in claim 2 in which the image data is modified to depict an image of bone tissue.

6. The method as recited in claim 5 in which the calculated corrections offset x-ray beam hardening effects due to bone tissue.

7. The method as recited in claim 2 in which steps a) through e) are repeated to further correct the CT image data.

8. The method as recited in claim 1 in which the image data is rotated by the angle $\beta$ as part of the reprojection.

9. The method as recited in claim 1 in which the image data and the set of parallel lines to which the image data is translated during the warping step are rotated by an angle $\beta$.

* * * * *